US011428959B2

(12) United States Patent
Le Saux (10) Patent No.: US 11,428,959 B2
(45) Date of Patent: Aug. 30, 2022

(54) METHOD AND APPARATUS FOR DETERMINING A REFERENCE HEAD POSTURE OF A SUBJECT

(71) Applicant: Essilor International, Charenton-le-Pont (FR)

(72) Inventor: Gilles Le Saux, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 16/761,628

(22) PCT Filed: Dec. 3, 2018

(86) PCT No.: PCT/EP2018/083380
§ 371 (c)(1),
(2) Date: May 5, 2020

(87) PCT Pub. No.: WO2019/110527
PCT Pub. Date: Jun. 13, 2019

(65) Prior Publication Data
US 2021/0181537 A1     Jun. 17, 2021

(30) Foreign Application Priority Data
Dec. 6, 2017    (EP) ..................... 17306716

(51) Int. Cl.
*G02C 13/00*     (2006.01)
*G06T 7/73*     (2017.01)
(Continued)

(52) U.S. Cl.
CPC .......... *G02C 13/005* (2013.01); *A61B 5/1114* (2013.01); *A61B 5/4561* (2013.01);
(Continued)

(58) Field of Classification Search
CPC combination set(s) only.
See application file for complete search history.

(56) References Cited

U.S. PATENT DOCUMENTS

2010/0128220 A1    5/2010   Chauveau
2012/0182521 A1    7/2012   Kubitza et al.
(Continued)

FOREIGN PATENT DOCUMENTS

DE    10 2014 013447     3/2016
JP    S55-133016 A    10/1980
(Continued)

OTHER PUBLICATIONS

International Search Report, PCT/EP2018/083380, dated Jan. 15, 2019.
(Continued)

*Primary Examiner* — Vikkram Bali
(74) *Attorney, Agent, or Firm* — Nixon & Vanderhye (57) ABSTRACT

Disclosed is a method for determining a subject's reference head posture, the method including: a) obtaining a movement or a position of at least one eyelid of the subject while he/she moves his/her head up and down starting from an initial head posture wherein he/she directs his/her gaze towards a predetermined direction, the subject keeping his/her gaze directed towards the predetermined direction during the motion of his/her head; and b) determining the reference head posture as a function of a movement or a position of at least one eyelid of the subject during the motion of his/her head at step a). Further disclosed is a method for measuring a distinctive height associated with a frame of a pair of spectacles worn by the subject, as well as a method for mounting and for verifying the mounting of an ophthalmic lens in a frame of a pair of spectacles.

13 Claims, 2 Drawing Sheets

(51) Int. Cl.
  *A61B 5/11*   (2006.01)
  *A61B 5/00*   (2006.01)
  *G06T 7/00*   (2017.01)
(52) U.S. Cl.
  CPC ............... *G06T 7/001* (2013.01); *G06T 7/73*
      (2017.01); *G06T 2207/10016* (2013.01); *G06T
                                 2207/30201* (2013.01)

(56) References Cited

U.S. PATENT DOCUMENTS

2015/0198822 A1   7/2015  Divo et al.
2019/0102905 A1*  4/2019  Skogo ...................... G06T 7/73

FOREIGN PATENT DOCUMENTS

JP      2010-524011 A    7/2010
KR   10-2013-0048765 A    5/2013
KR   10-2015-0143584 A   12/2015
WO     WO 2010/145736   12/2010

OTHER PUBLICATIONS

Written Opinion, PCT/EP2018/083380, dated Jan. 15, 2019.
Notice of Reasons for Rejection issued in JP Patent Application No. 2020-530491 dated Nov. 1, 2021, with English Translation provided.
Office Action issued in Korean Patent Application No. 10-2020-7012568 dated May 27, 2022.

* cited by examiner

Fig.7

METHOD AND APPARATUS FOR DETERMINING A REFERENCE HEAD POSTURE OF A SUBJECT

TECHNICAL FIELD OF THE INVENTION

The invention pertains to the domain of optometry and to the measurements of parameters relative to a subject wearing an ophthalmic lens.

More precisely, the invention relates to a method and apparatus for determining a reference head posture of a subject.

The invention also proposes a method for measuring a distinctive height associated with a frame of a pair of spectacles worn by the subject.

Further, the invention relates to a method for mounting and for verifying the mounting of an ophthalmic lens in a frame of a pair of spectacles.

BACKGROUND INFORMATION AND PRIOR ART

Numerous documents describe devices and methods for determining the head posture of a subject.

For example, document WO 2010/145736 provides an improved method for determining the head posture of a subject. The method of WO 2010/145736 comprises: recording the head posture of the subject over a certain period of time; and, determining a preferred, or "habitual", head posture from the recorded head posture.

This method prevent the habitual head posture of the subject from being mistakenly assumed as a head posture which is recorded or determined randomly at a point in time and which precisely does not correspond to the subject's usual head posture.

However, this method may be a tedious work for the eye-care practitioner who shall equip the subject with a device on his/her head or on his/her frame, and make a long video recording. Moreover, although the result of the measurement may be very precise, it is very variable from one day to the next.

SUMMARY OF THE INVENTION

Therefore one object of the disclosure is to provide a precise, reliable and simple method for determining a reference head posture of a subject which is precise and simple to implement by an eye-care practitioner, but which is also reliable and reproducible from one day to the next.

The above object is achieved according to the invention by providing a method comprising the steps of:

a) obtaining a movement or a position of at least one eyelid of the subject while he/she moves his/her head up and down starting from an initial head posture wherein he/she directs his/her gaze towards a predetermined direction, the subject keeping his/her gaze directed towards said predetermined direction during the motion of his/her head; and b) determining said reference head posture as a function of a movement or a position of at least one eyelid of the subject during the motion of his/her head at step a).

Indeed, it has been found by the Applicant that the head posture of the subject determined according to this method is very reliable and does not depend on the time the measurement is performed.

In particular, the method according to the invention allows determining a reference head posture which is very specific for each subject.

In a particular embodiment, said step a) of obtaining the movement or the position of at least one eyelid of the subject comprises asking the subject to:

a1) adopt an initial head posture wherein he/she directs his/her gaze towards a predetermined direction; and a2) move his/her head up and down starting from said initial head posture while keeping his/her gaze directed towards said predetermined direction.

Other advantageous and non limiting features of the method according to the invention are as follows:

at step b), the at least one eyelid of the subject is his/her upper eyelid;

the reference head posture is determined at step b) as the posture adopted by the subject at an instant where said at least one upper eyelid stops, respectively starts, moving when the head of the subject is moving down, respectively is moving up;

the reference head posture is determined at step b) as the posture adopted by the subject at an instant where said at least one upper eyelid fits in, respectively get out of, an arch of the corresponding eyebrow of the subject, when the head of the subject is moving up, respectively is moving down;

at step a), the predetermined direction is the subject's gaze direction when he/she is looking at a fixed point straight ahead or at himself/herself in a mirror or on a display screen;

at step b), said reference head posture is determined while observing at step a), visually or by means of a video camera, the movement and/or the position of said at least one eyelid of the subject.

A further object of the invention is to provide a measurement method which benefits from the determination of the reference head posture to allow making the measurement always in the same head posture of the subject.

Hence, the invention proposes a method for measuring a distinctive height associated with a frame of a pair of spectacles worn, physically or virtually, by said subject, said method comprising the steps of:

determining a reference head posture of the subject using a method of determination in accordance with the above-detailed invention; and when the head of the subject is in said reference head posture, determining a measured value of said distinctive height as a function of the distance, along a vertical direction substantially perpendicular to the initial predetermined direction, between a center of one pupil of the subject and a bottom edge of said frame.

Advantageously, one acquires, at step b), a tilt angle of the head of the subject with respect to said vertical direction; and one determines said distinctive height when the head of the subject is tilted with respect to said vertical direction by the acquired tilt angle.

Other advantageous and non limiting features of the measurement method according to the invention are as follows:

one determines a real value of said distinctive height with an offset to the measured value;

said offset depends on subject's ethnicity;

when the subject wears virtually said pair of spectacles, one positions said frame with respect to the head of the subject in accordance with a distance along said vertical direction between the eyebrows of the subject and a top edge of said frame; and one determines said measured value of the distinctive height in lighting conditions adapted to reduce the size of the pupil of the subject.

Another object of the invention is to provide a way to help and verify the mounting of a lens in a frame.

More precisely, the invention pertains to a method for verifying the mounting of at least one ophthalmic lens in a frame of a pair of spectacles designed to be worn by a subject, said method comprising the steps of:
- determining a reference head posture of the subject using a method of determination according to the invention;
- capturing a first image of the frame when the subject is in said reference head posture and wears said frame without the at least one ophthalmic lens;
- mounting in said frame the at least one ophthalmic lens having a marking;
- capturing a second image of the frame fitted with the at least one ophthalmic lens displaying said marking;
- processing said first and second images so as to superimpose the images of the frame in both images;
- determining a calculated value of the distance between said marking and a center of a pupil of an eye of the subject to be visually corrected with said ophthalmic lens;
- comparing said calculated value with a threshold value; and
- verifying the mounting of the at least one ophthalmic lens in the frame as a function of the previous comparison.

A further object of the invention is to provide an apparatus for determining a reference head posture of a subject comprising:
- receiving means adapted to receive a movement or a position of at least one eyelid of the subject while he/she moves his/her head up and down starting from an initial head posture wherein he/she directs his/her gaze towards a predetermined direction, the subject keeping his/her gaze directed towards said predetermined direction during the motion of his/her head; and
- image-processing means configured to analyze images or films captured by said image-capturing means and to determine said reference head posture as a function of at least one of a movement and a position of at least one eyelid of the subject.

In particular implementations, the apparatus further comprises image-capturing means adapted to capture the movement or position of the at least one eyelid of the subject and to provide it to the receiving means.

In a preferred embodiment, the apparatus according to the invention comprises eye-catching means arranged in front of the subject so that he/she adopts an initial head posture wherein he/she directs his/her gaze towards a predetermined direction.

In another embodiment, the eye-catching means are provided in addition to the apparatus of the invention.

Advantageously, the eye-catching means may comprise a light source positioned at a same height as the eyes of the subject.

Alternatively, the eye-catching means may comprise a mirror or a display screen positioned in front of the subject so that the predetermined direction is substantially horizontal.

In another preferred embodiment where said subject wearing physically or virtually a pair of spectacles, the apparatus according to the invention is such that:
- the receiving means are adapted to receive at least one image of the subject when his/her head is in said reference head posture; and
- the image-processing means are further configured to analyze said at least one image and to determine a measured value of a distinctive height associated with a frame of said pair of spectacles as a function of the distance, along a vertical direction substantially perpendicular to the initial predetermined direction, between a center of one pupil of the subject and a bottom edge of said frame.

In particular implementations with the image-capturing means, the latter are adapted to capture the image(s) of the subject when his/her head is in the reference head posture.

Advantageously, said image-capturing means have an optical axis parallel to a visual axis of the subject. This prevents the measurement to be distorted by a parallax error.

Another object of the invention is to provide an apparatus for determining a reference head posture of a subject, the apparatus comprising:
- at least one input adapted to receive at least one image representative of a movement or a position of at least one eyelid of the subject while a head of the subject moves up and down starting from an initial head posture in which a gaze of the subject is directed towards a predetermined direction, the gaze being maintained directed towards said predetermined direction during motion of the head; and
- at least one processor configured to analyze the at least one image received by said at least one input and to determine said reference head posture as a function of at least one of a movement and a position of at least one eyelid of the subject based on the analyzed at least one image.

In particular implementations, the apparatus further comprises an image-capturing device configured to capture the movement or position of the at least one eyelid of the subject and to provide it to the at least one input.

In a preferred embodiment of this apparatus, the at least one input is configured to receive the at least one image when the head is in said reference head posture; and the at least one processor is configured to analyze said at least one image and to determine a measured value of a distinctive height associated with a frame of said pair of spectacles as a function of the distance, along a vertical direction substantially perpendicular to the initial predetermined direction, between a center of one pupil of the subject and a bottom edge of said frame, when the subject is physically or virtually wearing a pair of spectacles.

In particular implementations with the image-capturing device, the latter is configured to capture the image(s) of the subject when his/her head is in the reference head posture.

The invention also relates to a software program product embodied in a non-transitory computer-readable medium configured to cause one or more processing devices to execute a method for determining a reference head posture of a subject, the method comprising:
a) obtaining a movement or a position of at least one eyelid of the subject while he/she moves his/her head up and down starting from an initial head posture wherein he/she directs his/her gaze towards a predetermined direction, the subject keeping his/her gaze directed towards said predetermined direction during the motion of his/her head; and
b) determining said reference head posture as a function of the movement or the position of said at least one eyelid of the subject during the motion of his/her head at step a).

The invention finally provides a software program product embodied in a non-transitory computer-readable medium configured to cause one or more processing devices to execute a method for determining a reference head posture of a subject, the method comprising:
a) receiving data representative of a movement or a position of at least one eyelid of a subject during a motion of a head of the subject up and down starting from an initial head posture of the subject in which a gaze of the subject is directed towards a predetermined direction, the gaze of the subject being kept directed towards the predetermined direction during the up and down motion; and b) determining said reference head posture as a function of the movement or the position of said at least one eyelid of the subject during the motion of the head, based on the received data.

DETAILED DESCRIPTION OF EXAMPLES

The following description made with reference to the accompanying drawings given by way of non-limiting example makes it clearly understood what the invention consists in and how it can be reduced to practice.

We will describe hereafter a method and apparatus for determining a reference head posture of a subject 1 (see FIG. 1) where one uses the position and/or the movement of one or both eyelids of the subject, while he (we will assume for the rest of the description that the subject is a man) moves his head.

This reference head posture, which is specific for each subject, is quite stable and does not vary very much from one day to the other.

Hence, determining the reference head posture of the subject 1 is particularly useful when carrying out optical and/or eye- or head-related measurements of the subject 1, in view of the design and manufacturing of eyeglasses, in particular for progressive addition lenses (PAL).

Figure 1:
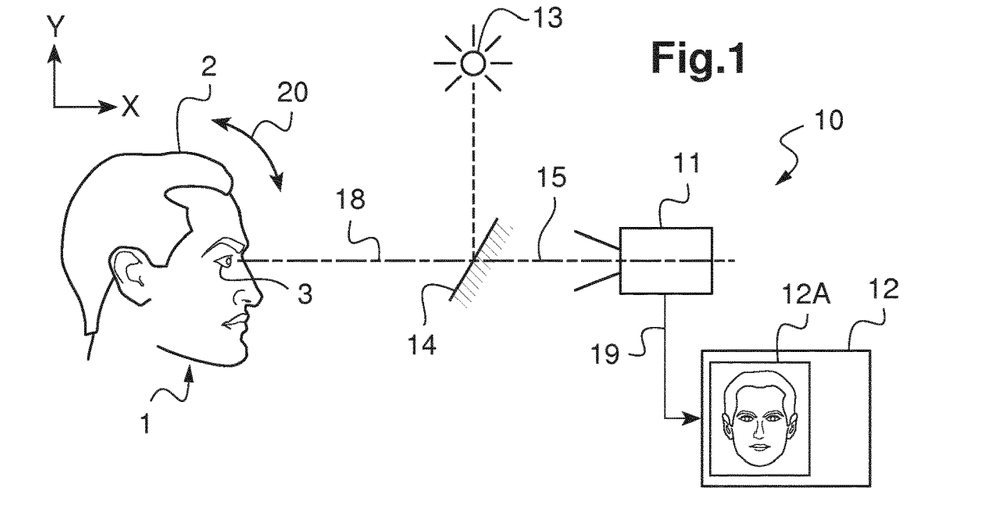
FIG. 1 is a schematic representation of a subject in front of an apparatus according to a first embodiment of the invention.

We represented on FIG. 1 an apparatus 10 according to a particular embodiment of the invention. The apparatus 10 comprises a digital video recorder 11 (hereinafter referred to as a camera) and a computer system 12, linked to the camera 10 by a digital cable 19 for 2-ways communication.

In this particular embodiment, the apparatus 10 further comprises eye-catching means 13, 14 arranged in front of the subject 1 so that he adopts an initial head posture wherein he directs his gaze 16, 17 towards a predetermined direction 18 (see FIG. 1A).

The eye-catching means 13, 14 comprise here a light source 13, e.g. a light-emitting diode (LED), and a semi-transparent or dichroic mirror 14 positioned and oriented in front of the subject 1 with respect to the light source 13 and the head 2 of the subject 1 so that the predetermined direction 18 is substantially horizontal, along the horizontal axis Y (see arrows in FIGS. 1 and 1A).

In other words, the LED 13 is placed just above/upright the mirror 14 which is tilted with a 45° angle relative to the vertical axis X so that the (virtual) image of the light source 13 is positioned on the horizontal axis Y (behind the mirror 14, near the camera 11), along the predetermined direction 18.

In a variant, the light source may be positioned at the same height as the eyes of the subject, so that the initial head posture is the one that the subject would adopt when looking at a far-distant point (far vision).

In another variants, the predetermined direction may be defined by the subject's gaze direction when he is looking at a fixed point straight ahead (a light source placed close to the camera 11) or at himself in a mirror or on a display screen, e.g. on the screen of his cell phone of his digital tablet.

The camera 11 is preferably positioned in front of the head 2 of the subject 1, behind the semi-transparent or dichroic mirror 14, and has an optical axis 15 which is preferably parallel to the visual axis 18 (see FIG. 1A) of the subject 1 (to avoid parallax issue when capturing the images of both eyes of the subject).

The camera 11 is optically and mechanically set up to capture images of the head 2 and the eyes 3, 4 of the subject 1 placed in front of the camera 11.

The computer system 12 may also includes a video screen 12 to monitor in real time the images or films recorded by the camera 11. The computer system 12 comprises calculation means suitable to analyze the images captured by the camera 11 and run image-processing algorithms to extract useful information from those images and determine the looked-for reference head posture as a function of a movement or a position of at least one eyelid of the subject.

Using the apparatus 10 of FIG. 1, it is possible to perform a method according to the invention, said method comprising the steps of:

a) asking the subject 1 to:
  a1) adopt an initial head posture wherein he directs his gaze towards the predetermined direction 18;
  a2) move his head up and down (see double arrow 20 on FIG. 1) starting from the initial head posture while keeping his gaze directed towards the predetermined direction 18; and b) determining the reference head posture as a function of a movement or a position of at least one eyelid of the subject 1 during the motion of his head at step a2).

Hence, at step a), one obtains a movement or a position of at least one eyelid of the subject while he/she moves his/her head up and down starting from an initial head posture wherein he/she directs his/her gaze towards a predetermined direction, the subject keeping his/her gaze directed towards said predetermined direction during the motion of his/her head.

Figure 3:
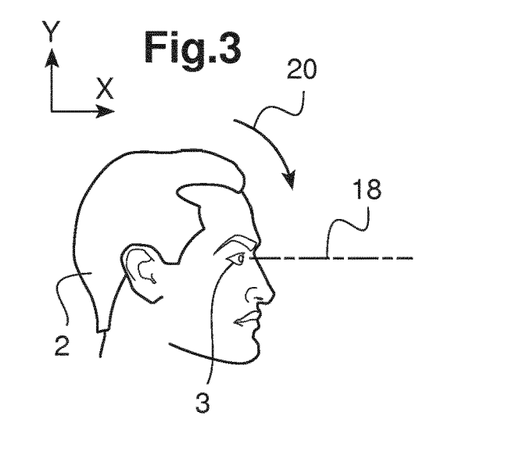
FIGS. 3 and 4 are schematic drawings of the head of the subject in the initial head posture and in the reference head posture respectively.
Figure 4:
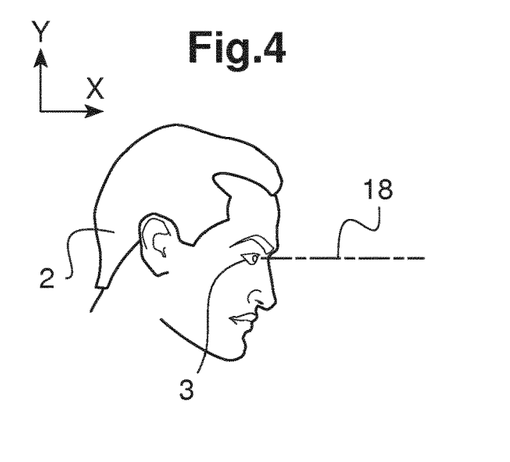

We have represented on FIGS. 3 and 4, the head 2 of the subject 1 when he is respectively in the initial head posture (case of FIG. 3) and in the reference head posture (case of FIG. 4).

Step a)

Figure 2:
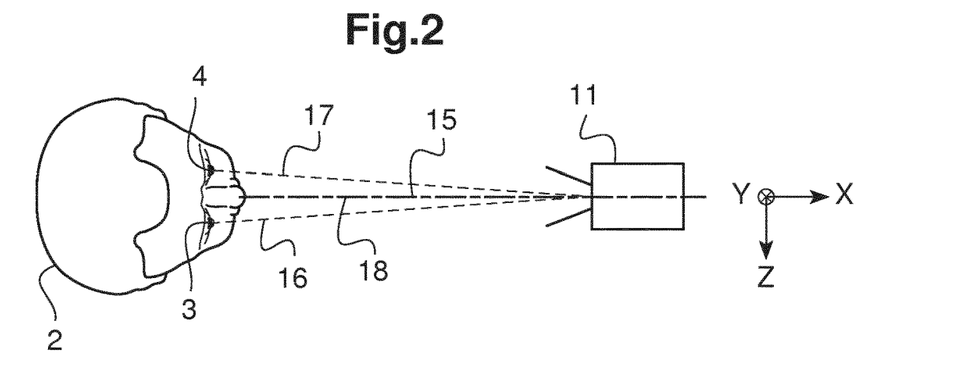
FIG. 2 is a top view of FIG. 1 showing both eyes of the subject.

At the beginning of the method, the subject 1 sits, or stands, in front of the apparatus 10 and tries to focus on the image of the light source 13 reflected by the mirror 14. In this situation, his gaze (i.e. the lines of sight 16, 17 in FIG. 2) is directed towards the image, defining the predetermined direction 18.

Figure 5:
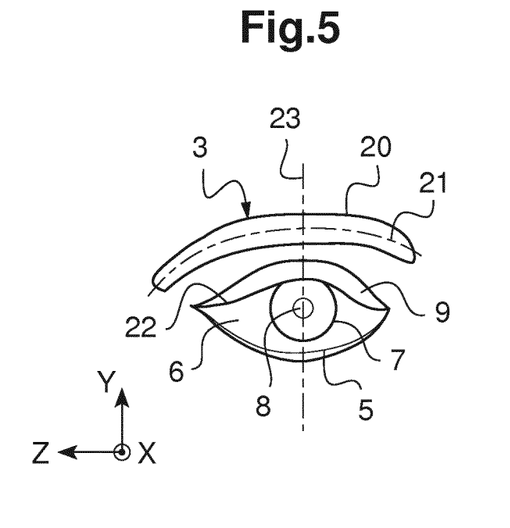
FIG. 5 is a schematic drawing of the eye of a subject showing his eyelids and the pupil of his eye in an initial head posture.

In this initial head posture (FIG. 3), we represented on FIG. 5 a detailed view of the (right) eye 3 of the subject 1 with:
  the lower eyelid 5 and the upper eyelid 9;
  the sclera 6;
  the iris 7 and the pupil 8.

In a preferred embodiment of the invention, the lighting conditions of the experiment is such that the subject 1 is in photopic conditions (high environment luminance level above roughly 300 cd/m$^2$) so that the pupil 8 of the eye 3 of the subject 1 is close to its minimum size (myosis), which is generally around 1.5 to 2 millimeters.

In practice here, the photopic conditions are obtained with ambient lighting (e.g. such as those usually found at an optical shop) and with the light level of the light source 13.

As shown on FIG. 5, the upper eyelid 9 of the right eye 3 is at this time lifted up, such that it only hides a small upper part of the iris 7, yet without vignetting the pupil 8.

In the initial head posture (FIGS. 3 and 5), one may acquire an image of the entire eye 3 of the subject 1, including the eyebrow 20 of the subject and the arch 21 of the eyebrow 20. Preferably, one can process the acquired image to identify the arch 21 and the edge 22 of the upper eyelid 9, and calculate an initial position of the upper eyelid 9 of the eye 3, defined by the distance, along the vertical axis 23 (parallel to axis X), from the arch 21 to the edge 22 of the upper eyelid 9.

Then, starting from the initial head posture (FIG. 3) where the subject 1 directs his gaze 16 in the predetermined direction 18, the subject 1 is asked to move his head 2 up and down (step a2; see double arrow 20 on FIG. 3) without stopping looking towards the image of the light source 13 and preferably without turning his head 2 to the left or to the right.

Step b)

During the whole motion of his head 2, the camera 11 of the apparatus 10 records, e.g. at a sampling rate of 30 or 60 Hz, the images of the eyes 3, 4 of the subject 1 and send the images to the computer system 12 for image processing and analysis.

The reference head posture (see FIG. 4) is then determined as a function of the movement or the position of the upper eyelid 9 of the subject 1 during the motion of his head 2.

In an alternative embodiment, the lower eyelid 5 may be used in the images of the eye of the subject.

Figure 6:
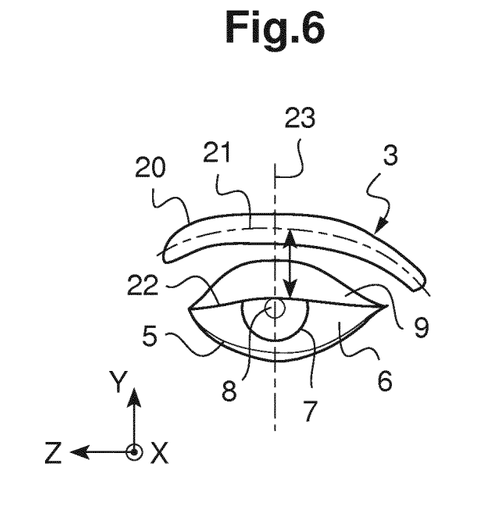
FIG. 6 is a schematic drawing of the eye of FIG. 5 in the reference head posture.

As shown in FIG. 6, in the reference head posture, the upper eyelid 9 is here lowered with respect to its initial position (initial head posture of FIG. 3) such that it hides almost one half of the iris 7 (see above).

In the reference head posture (FIG. 4), one may also calculate a "reference" position of the upper eyelid 9 of the eye 3, defined again by the distance, along the vertical axis 23 (parallel to axis X), from the arch 21 to the edge 22 of the upper eyelid 9 (see FIG. 6).

In particular embodiments of the method according to the invention, the reference head posture is determined at step b) as the posture adopted by the subject 1 at an instant where the upper eyelid 9 fits in, or respectively gets out of, the arch 21 of the corresponding eyebrow 20 of the subject 1, when the head 2 of the subject 1 is moving down, respectively is moving up.

When the reference head posture is located thanks to the movement of the upper eyelid 9, it is determined at step b) as the head posture adopted by the subject 1 at an instant where the upper eyelid 9 stops, respectively starts, moving when the head 2 of the subject 1 is moving up, respectively is moving down.

The reference head posture may be determined either with the video camera 11 (cases of FIGS. 4 and 6) or directly by a visual observation. In case of visual observation, one may equip the subject with a special device recording the inclination angle of the head of the subject. The eye-care practitioner (ECP) who carries the method then notes the inclination angle corresponding to the reference head posture of the subject.

Then, in order to reproduce the reference head posture, determined previously with the method, it is possible to fit the head 2 of the subject 1 (if he doesn't wear a frame) or the frame he wears with the above inclination device; and ask the subject 1 to tilt his head 2 until the inclination angle equalize the value determined during the previous measurement.

The above-detailed apparatus 10 and method may be used/implemented when the subject is wearing, or not, eyeglasses with a frame, with or without an ophthalmic lens fitted in the frame. Those eyeglasses may be the one he usually wears or a new one he chose.

The above apparatus and method are particularly interesting in order to take various measurements on the subject 1 when he is in the reference head posture, as the reference head posture is kind of specific of the subject 1 in determined conditions.

Figure 7:
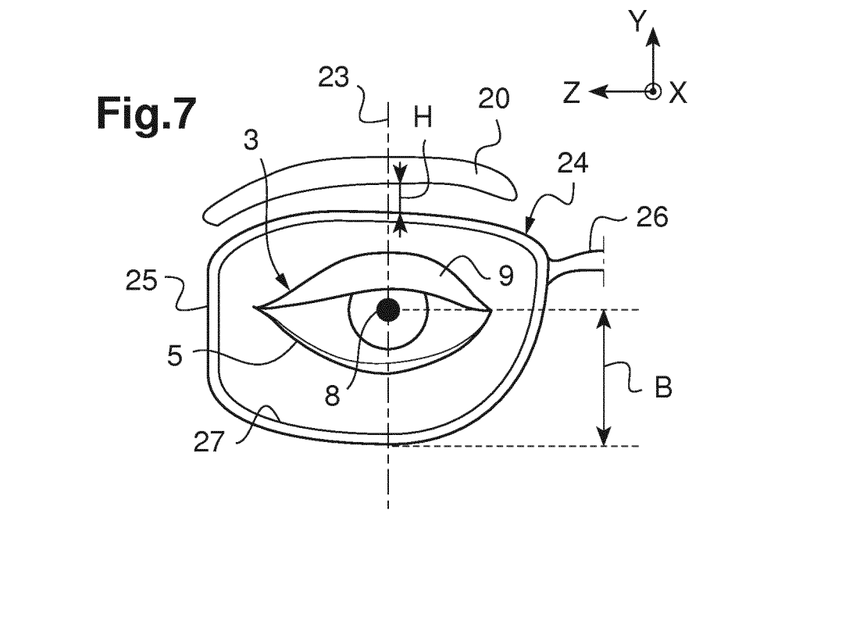
FIG. 7 is a schematic representation of an eye of a subject wearing frame of a pair of spectacles, with a detail on the fitting height between the bottom of the frame and the center of the pupil.

It is specifically interesting when it comes to measure geometric and/or morphological distances or lengths on the eye 2 of the subject 1 wearing a frame of a pair of spectacles. More precisely, with reference to FIG. 7, the invention proposes also a method for measuring a distinctive height, hereinafter referred to as fitting height B, associated with a frame 24 of a pair of spectacles worn, physically or virtually, by the subject 1.

Said measuring method comprises the steps of:
  determining the reference head posture of the subject 1 using a method of determination according to the invention (see above); and
  when the head 2 of the subject 1 is in this reference head posture, determining a measured value B of the fitting height as a function of the distance, along a vertical direction X substantially perpendicular to the initial predetermined direction 18 (see FIG. 2), between a center 28 of a pupil 8 of the subject 1 and a bottom edge 27 of said frame 24.

In order to determine the measured value of the fitting height B, one can use the same apparatus 10 as in FIG. 10. In this case, the computer system 12 is then configured to process the images of the head 2 and of the eyes 3, 4 of the subject 1 captured by the camera 11 in order to detect both the pupil 8 of the eye 3 and the circle 25 of the frame 24 (when said frame comprises two circles 25 linked by a bridge 26, see FIG. 10).

Once the pupil 8 and the circle 25 are detected, the center 28 of the pupil 28 and the inner edge 26 of circle 25 can be determined, and the distance, i.e. the distinctive height, along the vertical axis X between the center 28 and the edge 26.

Advantageously, one acquires, at step b) of the method of determination, a tilt angle of the head 2 of the subject 1 with respect to the vertical direction 23; and one determines the fitting height when the head 2 of the subject 1 is tilted with respect to the vertical direction X by the acquired tilt angle $\theta_T$.

In a preferred embodiment of the invention, one determines a real value $B_R$ of said fitting height with an offset $\delta B$ to the measured value B, the offset depending for example on subject's ethnicity: Caucasian, Eurasian, Asian, etc . . . .

The value $\delta B$ of the offset may be, for example, the average angular difference of the inclination angle (measured by an inclination device) measured between the reference head posture and a natural head posture of the subject.

In another preferred embodiment, one determines the measured value B of the fitting height in lighting conditions adapted to reduce the size of the pupil 8 of the subject 1. In those lighting conditions, the smaller size of the pupil 8 (due to the myosis of the iris 7) allows reaching a better precision in the determination of the center 28 of the pupil 8.

When the subject 1 wears virtually the pair of spectacles (i.e. a virtual frame is digitally added by the computer system 12 to the images of the head 2 of the subject 1 recorded by the camera 11), one positions the frame 24 with respect to the head 2 of the subject 1 in accordance with a distance H (see FIG. 7) along a vertical direction 23 (X axis) between the eyebrows 20 of the subject 1 and a top edge 29 of said frame 25.

The above apparatus 10 and method for determining the reference head posture of the subject 1 may be also used/implemented for a method for verifying the mounting of at least one ophthalmic lens in a frame of a pair of spectacles designed to be worn by the subject.

This advantageous method comprises the steps of:
determining the reference head posture of the subject 1 using a method of determination according to the invention (see above);
capturing a first image of the frame when the subject is in the reference head posture and wears the frame without the at least one ophthalmic lens;
mounting in the frame the at least one ophthalmic lens having a marking;
capturing a second image of the frame fitted with the at least one ophthalmic lens displaying said marking;
processing said first and second images so as to superimpose the images of the frame in both images;
determining a calculated value of the distance between said marking and a center of a pupil of an eye of the subject to be visually corrected with the ophthalmic lens.
comparing said calculated value with a threshold value; and
verifying the mounting of the at least one ophthalmic lens in the frame as a function of the previous comparison.

The basic principles of this measurement are as follows.

First, after the subject has chosen the eyeglasses frame he wants and after having adjusted this frame (without the ophthalmic lenses) on his head, one may ask the subject 1 to adopt an initial head posture (see step a1 above) where he directs his gaze towards a predetermined direction. In this first configuration, one acquires a first image of the face of the subject. This first image is processed, for example to determine the measured values of the inter-pupillary distance and of the fitting height between the center of pupils and the bottom edges of the frame (see details above). The first image and the value of the fitting height are provided to an operator which is responsible for the mounting of the ophthalmic lens(es) in the frame.

Then, this operator fits the one or two prescribed ophthalmic lenses in the selected frame. Like it is well known in the field, this fitting is done on the basis of the optical and geometric parameters of the lenses and of the geometric and morphological values previously measured (inter-pupillary distance, distinctive height, etc . . . ). In this second configuration, one acquires the second image of the frame fitted with the ophthalmic lenses, taking care that the usual fitting marks (marking) present on the lenses for mounting are visible on this second image.

Then, by digital processing, one tries superimposing, in a third image, the first and second images by modifying the size and/or shape of the image of the frame in the first image.

In this third image, still by numerical analysis of images, one calculates (or visually evaluates on a screen where the third image is displayed) the value of the distance between the marking and the left/right center of the pupil of the eye of the subject.

If the mounting is correct, then the calculated value should be smaller than a predetermined threshold value. On the contrary, if the calculated value is larger than the threshold value then the mounting of the ophthalmic lenses in the frame are not verified, and e.g. a corrective mounting operation can be performed by the operator.

Aspects of at least one embodiment can be embodied as a software program product or computer-readable code embodied on a non-transitory computer-readable medium, where the non-transitory computer-readable medium can cause one or more processors to perform operations, for example. The non-transitory computer-readable medium may be a computer-readable storage medium, which is any data storage device that can store data which can be thereafter read by a computer system or computer code processing apparatus. Examples of the computer-readable storage medium include read-only memory (ROM), random-access memory (RAM), CD-ROMs, magnetic tapes, floppy disks, and optical data storage devices. The software program product can also be distributed over network-coupled computer systems so that the computer-readable code is stored and executed by one or more processors in a distributed fashion.

The invention claimed is:

1. A method for determining a reference head posture of a head of a subject, said method comprising the steps of:
   a) obtaining a movement or a position of at least one upper eyelid of the subject while the subject moves the head of the subject up and down starting from an initial head posture in which a gaze of the subject is directed towards a predetermined direction, the subject keeping the gaze of the subject directed towards said predetermined direction during motion of the head of the subject, the predetermined direction being a gaze direction of the subject when the subject is looking at a fixed point straight ahead or at the subject in a mirror or on a display screen; and
   b) determining said reference head posture as a function of the movement or the position of said at least one upper eyelid of the subject during the motion of the head of the subject, the reference head posture being adopted by the subject at one of the following instants:
      a first instant where the at least one upper eyelid stops moving when the head of the subject is moving up,
      a second instant where the at least one upper eyelid starts moving when the head of the subject is moving down,
      a third instant where the at least one upper eyelid fits in an arch of a corresponding eyebrow of the subject when the head of the subject is moving down, and
      a fourth instant where the at least one upper eyelid is not in the arch of the corresponding eyebrow of the subject when the head of the subject is moving up.

2. The method according to claim 1, wherein said reference head posture is determined while observing, visually or by a video camera, one or more of the movement and the position of said at least one eyelid of the subject.

3. A method for measuring a distinctive height associated with a frame of a pair of spectacles worn, physically or virtually, by a subject, said method comprising:

determining the reference head posture of the subject using the method of determination according to claim 1; and when the head of the subject is in said reference head posture, determining a measured value of said distinctive height as a function of the distance, along a vertical direction substantially perpendicular to the initial predetermined direction, between a center of one pupil of the subject and a bottom edge of said frame.

4. The method according to claim 3, further comprising:
acquiring a tilt angle of the head of the subject with respect to said vertical direction; and
determining said distinctive height when the head of the subject is tilted with respect to said vertical direction by the acquired tilt angle.

5. The method according to claim 3, further comprising determining a real value of said distinctive height with an offset to the measured value.

6. The method according to claim 3, wherein, when the subject virtually wears said pair of spectacles, said frame is positioned with respect to the head of the subject in accordance with a distance along said vertical direction between the eyebrows of the subject and a top edge of said frame.

7. The method according to claim 3, further comprising determined said measured value of the distinctive height in lighting conditions adapted to reduce the size of the pupil of the subject.

8. A method for verifying mounting of at least one ophthalmic lens in a frame of a pair of spectacles configured to be worn by a subject, said method comprising:
determining the reference head posture of the subject using the method of determination according to claim 1;
capturing a first image of the frame when the subject is in said reference head posture and wears said frame without the at least one ophthalmic lens;
mounting the at least one ophthalmic lens having a marking in the frame;
capturing a second image of the frame fitted with the at least one ophthalmic lens displaying said marking;
processing said first and second images to superimpose the first and second images of the frame in both the first and second images;
determining a calculated value of the distance between said marking and a center of a pupil of an eye of the subject to be visually corrected with said ophthalmic lens;
comparing said calculated value with a threshold value; and
verifying the mounting of the at least one ophthalmic lens in the frame as a function of a previous comparison.

9. An apparatus for determining a reference head posture of a subject, the apparatus comprising:
an image-capturing device configured to capture at least one image representative of a movement or a position of at least one upper eyelid of the subject while the subject moves the head of the subject up and down starting from an initial head posture in which a gaze of the subject is directed towards a predetermined direction, the subject keeping the gaze of the subject directed towards said predetermined direction during motion of the head of the subject, the predetermined direction being a gaze direction of the subject when the subject is looking at a fixed point straight ahead or at the subject in a mirror or on a display screen; and
at least one processor configured to analyze images or films captured by the image-capturing device and to determine said reference head posture as a function of at least one of the movement and the position of the at least one upper eyelid of the subject, the reference head posture being adopted by the subject at one of the following instants:
a first instant where the at least one upper eyelid stops moving when the head of the subject is moving up,
a second instant where the at least one upper eyelid starts moving when the head of the subject is moving down,
a third instant where the at least one upper eyelid fits in an arch of a corresponding eyebrow of the subject when the head of the subject is moving down, and
a fourth instant where the at least one upper eyelid is not in the arch of the corresponding eyebrow of the subject when the head of the subject is moving up.

10. The apparatus according to claim 9, wherein, when said subject is physically or virtually wearing a pair of spectacles:
the image-capturing device is configured to capture the at least one image of the subject when the head of the subject is in said reference head posture, and
the at least one processor is configured to analyze said at least one image and to determine a measured value of a distinctive height associated with a frame of said pair of spectacles as a function of the distance, along a vertical direction substantially perpendicular to the initial predetermined direction, between a center of one pupil of the subject and a bottom edge of said frame.

11. The apparatus according to claim 9, further comprising a lighting system comprising a light source, the lighting system being configured to reflect an image of the light source at a position in relation to the light-capturing device to cause the subject to direct the gaze toward the predetermined direction.

12. The apparatus according to claim 9, wherein the lighting system further comprises a mirror configured to be oriented in front of the subject with respect to the image-capturing device such that a reflected light source image is configured to be viewed by the subject.

13. A non-transitory computer-readable medium on which is stored a computer program which, when executed by one or more processing devices, causes the one or more processing devices to execute a method for determining a reference head posture of a head of a subject, the method comprising:
a) obtaining a movement or a position of at least one upper eyelid of the subject while the subject moves the head of the subject up and down starting from an initial head posture in which a gaze of the subject is directed towards a predetermined direction, the subject keeping the gaze of the subject directed towards said predetermined direction during motion of the head of the subject, the predetermined direction being a gaze direction of the subject when the subject is looking at a fixed point straight ahead or at the subject in a mirror or on a display screen; and
b) determining said reference head posture as a function of the movement or the position of said at least one upper eyelid of the subject during the motion of the head of the subject, the reference head posture being adopted by the subject at one of the following instants:
a first instant where the at least one upper eyelid stops moving when the head of the subject is moving up,
a second instant where the at least one upper eyelid starts moving when the head of the subject is moving down, a third instant where the at least one upper eyelid fits in an arch of a corresponding eyebrow of the subject when the head of the subject is moving down, and a fourth instant where the at least one upper eyelid is not in the arch of the corresponding eyebrow of the subject when the head of the subject is moving up.

\* \* \* \* \*